(12) United States Patent
Mahajan et al.

(10) Patent No.: US 9,307,920 B2
(45) Date of Patent: Apr. 12, 2016

(54) METHOD AND APPARATUS FOR AUTOMATIC ARRHYTHMIA CLASSIFICATION WITH CONFIDENCE ESTIMATION

(71) Applicant: Cardiac Pacemakers, Inc., St. Paul, MN (US)

(72) Inventors: Deepa Mahajan, Circle Pines, MN (US); Christopher Pulliam, South Euclid, OH (US); Yanting Dong, Lexington, KY (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 253 days.

(21) Appl. No.: 13/864,023

(22) Filed: Apr. 16, 2013

(65) Prior Publication Data

US 2013/0274624 A1 Oct. 17, 2013

Related U.S. Application Data

(60) Provisional application No. 61/625,471, filed on Apr. 17, 2012.

(51) Int. Cl.
| | |
|---|---|
| A61B 5/0402 | (2006.01) |
| G09B 23/28 | (2006.01) |
| A61B 5/04 | (2006.01) |
| A61B 5/0464 | (2006.01) |
| A61B 5/00 | (2006.01) |
| A61N 1/362 | (2006.01) |
| A61N 1/39 | (2006.01) |
| A61N 1/36 | (2006.01) |

(52) U.S. Cl.
CPC ............ *A61B 5/04012* (2013.01); *A61B 5/0464* (2013.01); *A61B 5/7267* (2013.01); *A61B 5/7275* (2013.01); *A61N 1/3622* (2013.01); *A61B 5/0031* (2013.01); *A61N 1/3605* (2013.01); *A61N 1/3956* (2013.01)

(58) Field of Classification Search
USPC ................................................. 600/515, 518
See application file for complete search history.

(56) References Cited

U.S. PATENT DOCUMENTS

| | | | |
|---|---|---|---|
| 7,672,491 | B2 | 3/2010 | Krishnan et al. |
| 7,742,641 | B2 | 6/2010 | Ivanov et al. |
| 7,912,528 | B2 | 3/2011 | Krishnan et al. |
| 2010/0106036 | A1* | 4/2010 | Dong et al. ................... 600/523 |
| 2010/0280841 | A1 | 11/2010 | Dong et al. |

OTHER PUBLICATIONS

Dong, Yanting, et al., "Adjudication of Arrhythmia Episode Data Systems and Methods", U.S. Appl. No. 61/175,232, filed May 4, 2009.
Polikar, R, "Ensemble Based Systems in Decision Making", IEEE Circuits and Systems Magazine, vol. 6, No. 3, (2006), 21-45.
Witten, I. H., et al., "Data Mining—Practical Machine Learning Tools and Techniques", Third Edition, Morgan Kaufmann Publishers, Burlington, MA, (Part 1 of 2t), (2011), 300 pgs.
Witten, I. H., et al., "Data Mining—Practical Machine Learning Tools and Techniques", Third Edition, Morgan Kaufmann Publishers, Burlington, MA, (Part 2 of 2), (2011), 346 pgs.

* cited by examiner

*Primary Examiner* — Carl H Layno
*Assistant Examiner* — Jon Eric C Morales
(74) *Attorney, Agent, or Firm* — Faegre Baker Daniels LLP

(57) ABSTRACT

An arrhythmia classification system receives cardiac data from an implantable medical device, performs automatic adjudication of each cardiac arrhythmia episode indicated by the cardiac data, and generates episode data representative of information associated with the episode. The episode data include at least an episode classification resulting from the automatic adjudication of the episode and a confidence level in the episode classification. In one embodiment, the episode data further include key features rationalizing the automatic adjudication of the episode.

18 Claims, 11 Drawing Sheets

METHOD AND APPARATUS FOR AUTOMATIC ARRHYTHMIA CLASSIFICATION WITH CONFIDENCE ESTIMATION

CLAIM OF PRIORITY

This application claims the benefit of priority under 35 U.S.C. §119(e) of Mahajan et al., U.S. Provisional Patent Application Ser. No. 61/625,471, entitled "METHOD AND APPARATUS FOR AUTOMATIC ARRHYTHMIA CLASSIFICATION WITH CONFIDENCE ESTIMATION", filed on Apr. 17, 2012, which is herein incorporated by reference in its entirety.

TECHNICAL FIELD

This document relates generally to cardiac rhythm management systems and particularly to an arrhythmia adjudication system that classifies cardiac arrhythmia episodes and generates a confidence level in the classification of each of the arrhythmia episodes.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachyarrhythmia occurs when the heart contracts at a rate higher than a normal heart rate. Tachyarrhythmia generally includes ventricular tachyarrhythmia (VT) and supraventricular tachyarrhythmia (SVT). VT occurs, for example, when a pathological conduction loop forms in the ventricles through which electrical impulses travel circularly within the ventricles, or when a pathologically formed electrical focus generates electrical impulses from the ventricles. SVT includes physiological sinus tachyarrhythmia and pathologic SVTs. The physiological sinus tachyarrhythmia occurs when the SA node generates the electrical impulses at a particularly high rate. A pathologic SVT occurs, for example, when a pathological conduction loop forms in an atrium. Fibrillation occurs when the heart contracts at a tachyarrhythmia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as a SVT with an irregular rhythm, though not directly life threatening, also needs medical treatment such as atrial defibrillation to restore a normal cardiac function and to prevent the deterioration of the heart.

Implantable cardioverter-defibrillators (ICDs) are used to treat tachyarrhythmias, including fibrillation. To deliver an effective cardioversion-defibrillation therapy, an ICD automatically classifies each tachyarrhythmia by its type and/or origin. One example of arrhythmia classification performed by an ICD is morphology-based classification that determines the origin of a detected tachyarrhythmia episode by analyzing a correlation between morphological features of a cardiac signal sensed during the tachyarrhythmia episode and morphological features of a template signal sensed during a known type rhythm. However, morphological changes of a cardiac signal during a tachyarrhythmia episode may differ from patient to patient, as well as from time to time. Additionally, variations in the morphological features may also attribute to changes in other physiological factors. Therefore, there is a need for analyzing the ICD's classification of each tachyarrhythmia episode to allow for accurate diagnosis of the patient's conditions and evaluation of the ICD's performance.

SUMMARY

An arrhythmia classification system receives cardiac data from an implantable medical device, performs automatic adjudication of each cardiac arrhythmia episode indicated by the cardiac data, and generates episode data representative of information associated with the episode. The episode data include at least an episode classification resulting from the automatic adjudication of the episode and a confidence level in the episode classification. In one embodiment, the episode data further include key features rationalizing the automatic adjudication of the episode.

In one embodiment, a system is configured to be communicatively coupled to an implantable medical device. The implantable medical device senses one or more cardiac signals indicative of one or more arrhythmia episodes and produces cardiac data representative of the one or more cardiac signals. The system includes an arrhythmia analysis circuit, a memory circuit, and a user interface. The arrhythmia analysis circuit is configured to receive cardiac data transmitted from the implantable medical device, perform automatic adjudication of each episode of one or more arrhythmia episodes using the cardiac data, and generate episode data representative of information associated with the episode. The episode data include an episode classification resulting from the automatic adjudication of the episode and a confidence level in the episode classification. The memory circuit is configured to store data including the cardiac data and the episode data. The user interface includes a presentation device configured to present the information associated with the each episode.

In one embodiment, a method for classifying cardiac arrhythmias is provided. Cardiac data representative of the one or more cardiac signals sensed by an implantable medical device are received. The one or more cardiac signals are indicative of one or more arrhythmia episodes. Automatic adjudication of each episode of one or more arrhythmia episodes is performed using the cardiac data. Episode data representative of information associated with the episode are generated. The episode data include an episode classification resulting from the automatic adjudication of the episode and a confidence level in the episode classification. The cardiac data and the episode data are stored in a memory device. The information associated with the episode is presented to a user such as a physician or other caregiver.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this disclosure are not necessarily to the same embodiment, and such references contemplate more than one embodiment.

This document discusses, among other things, an external system communicating with an implantable medical device and retrospectively adjudicating arrhythmia episodes using data acquired and recorded by the implantable medical device. In various embodiments, the implantable medical device includes an implantable cardioverter-defibrillator (ICD). Automatic arrhythmia adjudication algorithms have been used to retrospectively classify arrhythmia episodes recorded by an ICD. Due to the complicated nature of cardiac signals representative of these arrhythmia episodes, sometimes physicians disagree on the classification of an arrhythmia episode. Such disagreements are also reflected in the performance of automatic arrhythmia adjudication algorithms when executed by the external system. In addition to providing the classification, the present external system provides its user, such as a physician or other caregiver, with information indicative of confidence in the classification and/or justification of the classification. Examples of such information include a confidence level associated with the classification, potential alternative classification, and/or information explaining rationale behind the classification decision.

Figure 1:
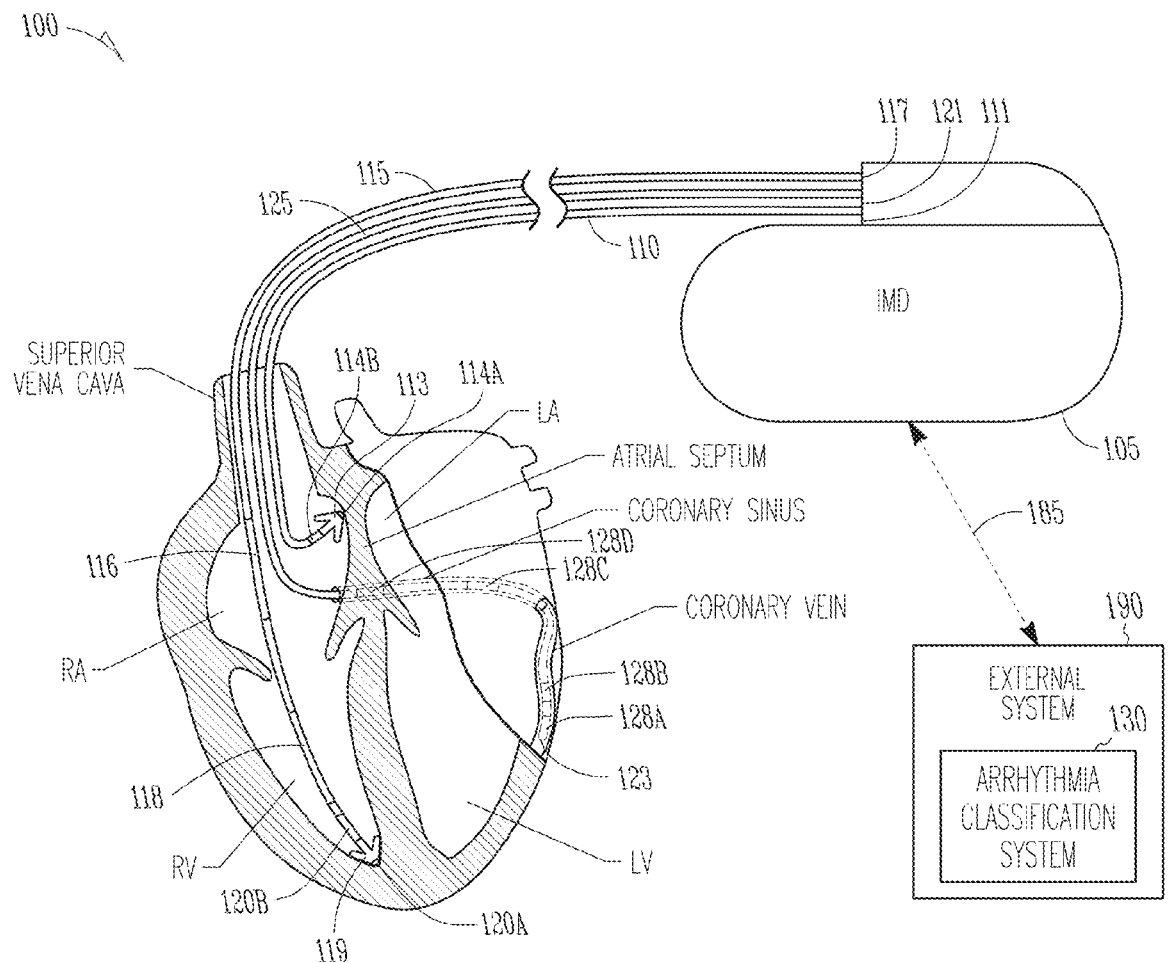
FIG. 1 is an illustration of an embodiment of a cardiac rhythm management (CRM) system including an implantable medical device and an external system and portions of an environment in which the CRM system operates.

FIG. 1 is an illustration of an embodiment of a cardiac rhythm management (CRM) system 100 and portions of an environment in which system 100 operates. CRM system 100 includes an implantable medical device (IMD) 105 that is electrically coupled to a heart through implantable leads 110, 115, and 125. An external system 190 communicates with IMD 105 via a telemetry link 185.

IMD 105 includes a hermetically sealed can housing an electronic circuit that senses physiological signals and delivers therapeutic electrical pulses. The hermetically sealed can also functions as an electrode (referred to as "the can electrode" hereinafter) for sensing and/or pulse delivery purposes. IMD 105 senses one or more cardiac signals indicative of one or more arrhythmia episodes and generates cardiac data representative of the one or more cardiac signals. In one embodiment, IMD 105 includes a pacemaker that delivers cardiac pacing therapies. In another embodiment, IMD 105 includes the pacemaker and a cardioverter/defibrillator that delivers cardioversion/defibrillation therapies. In various embodiments, IMD 105 includes one or more devices selected from monitoring devices and therapeutic devices such as the pacemaker, the cardioverter/defibrillator, a neurostimulator, a drug delivery device, and a biological therapy device. In one embodiment, the pacemaker provides for CRT.

Lead 110 is a right atrial (RA) pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations and delivering RA pacing pulses.

Lead 115 is a right ventricular (RV) pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations and delivering RV pacing pulses. In various embodiments, proximal defibrillation electrode 116 and/or distal defibrillation electrode 118 may also be used for sensing the RV electrogram.

Lead 125 is a left ventricular (LV) coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes an LV tip electrode 128A, a distal LV ring electrode 128B, and two proximal LV ring electrodes 128C and 128D. The distal portion of lead 125 is configured for placement in the coronary sinus and coronary vein such that LV electrodes 128A and 128B are placed in the coronary vein, and LV electrodes 128C and 128D are placed in or near the coronary sinus. LV electrodes 128A and 128B are incorporated into the lead body at distal end 123 and are each electrically coupled to IMD 105 through a conductor extending within the lead body. LV tip electrode 128A, distal LV ring electrode 128B, proximal LV ring electrode 128C, proximal LV ring electrode 128D, and/or the can electrode allow for sensing an LV electrogram indicative of LV depolarizations and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs. In various embodiments, IMD 105 senses the one or more cardiac signals using any combination of electrodes, such as those illustrated in FIG. 1, that is suitable for detection and classification of the one or more arrhythmia episodes.

External system 190 allows for programming of IMD 105 and receives signals acquired by IMD 105. In one embodiment, external system 190 includes a programmer. In another embodiment, external system 190 includes a patient monitoring system such as the system discussed below with reference to FIG. 3. In one embodiment, telemetry link 185 is an inductive telemetry link. In an alternative embodiment, telemetry link 185 is a far-field radio-frequency telemetry link. Telemetry link 185 provides for data transmission from IMD 105 to external system 190. This may include, for example, transmitting real-time physiological data acquired by IMD 105, extracting physiological data acquired by and stored in IMD 105, extracting therapy history data stored in IMD 105, and extracting data indicating an operational status of IMD 105 (e.g., battery status and lead impedance). The physiological data include the cardiac data representative of the one or more cardiac signals. Telemetry link 185 also provides for data transmission from external system 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing the tachyarrhythmia detection method discussed in this document), and programming IMD 105 to deliver pacing and/or cardioversion/defibrillation therapies.

External system 190 includes an arrhythmia classification system 130 that performs automatic adjudication of arrhythmia episodes using the cardiac data acquired by and telemetered from IMD 105. In various embodiments, arrhythmia classification system 130 generates episode data for each arrhythmia episode. The episode data includes data representative of information associated with the arrhythmia episode, including an episode classification resulting from the automatic adjudication of each arrhythmia episode and a confidence level in the episode classification. In various embodiments, arrhythmia classification system 130 also generates episode features including key features rationalizing the automatic adjudication of the arrhythmia episode. In various embodiments, episode information including the episode classification, the confidence level in the episode classification, and the key features rationalizing the automatic adjudication of the arrhythmia episode are presented to the user.

The circuit of CRM system 100 may be implemented using a combination of hardware and software. In various embodiments, each element of IMD 105 and external system 190, as illustrated in FIGS. 1-5, including its various embodiments, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof.

Figure 2:
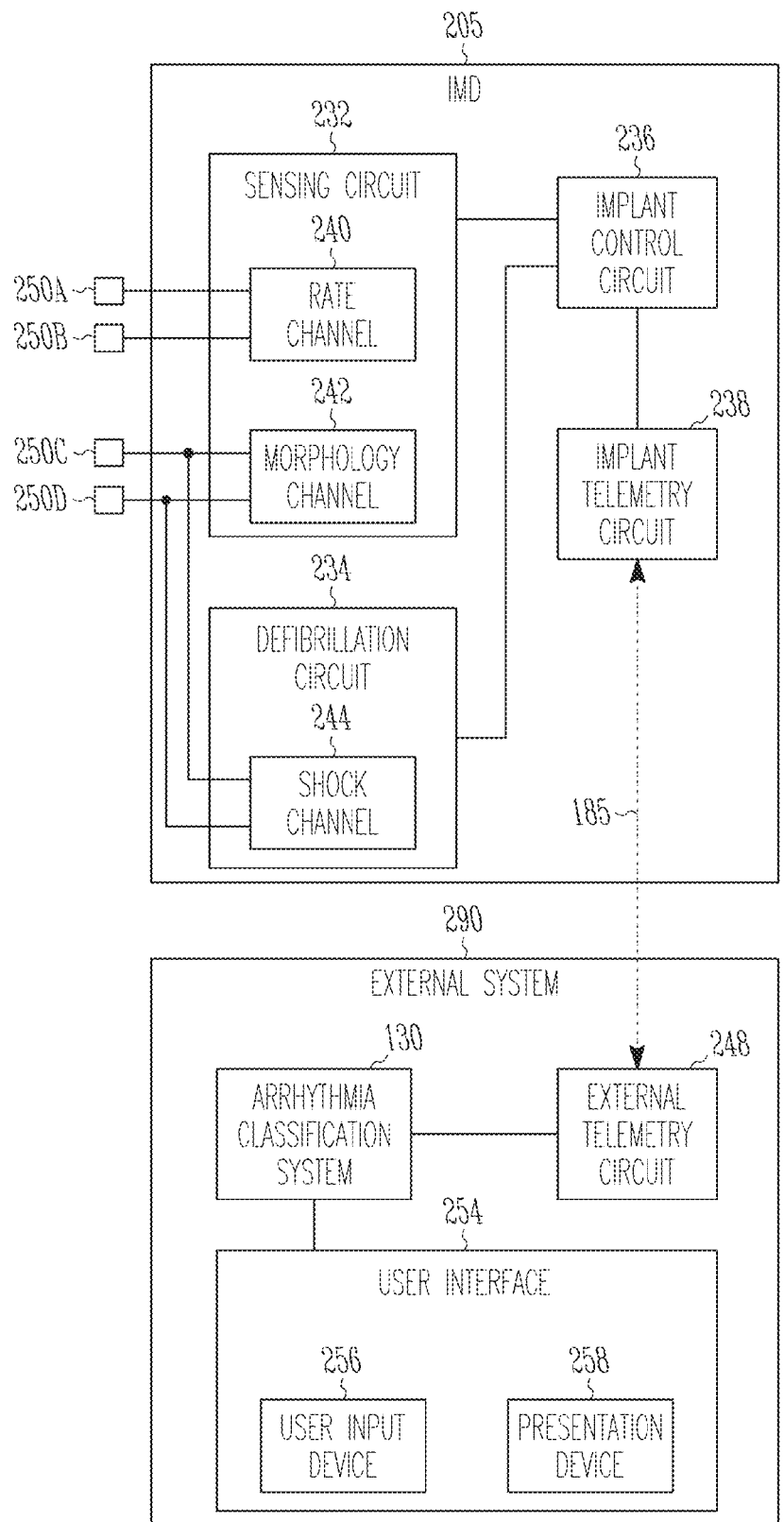
FIG. 2 is a block diagram illustrating an embodiment of portions of a circuit of the implantable medical device and portions of a circuit of the external system.

FIG. 2 is a block diagram illustrating an embodiment of portions of a circuit of IMD 205 and portions of a circuit of an external system 290. IMD 205 represents an embodiment of IMD 105 and includes a sensing circuit 232, a defibrillation circuit 234, an implant control circuit 236, and an implant telemetry circuit 238. In one embodiment, IMD 205 is an ICD. Sensing circuit 232 includes a rate channel 240 and a morphology channel 242. Rate channel 240 senses a regional cardiac signal through electrodes 250A and 250B for use in heart beat detection. Morphology channel 242 senses a global cardiac signal through electrodes 250C and 250D for use in morphological analysis. In one embodiment, rate channel 240 senses a regional ventricular electrogram through an RV tip electrode such as electrode 120A and an RV coil electrode such as electrode 118, and morphology channel 242 senses a global ventricular electrogram through the RV coil electrode and an SVC coil electrode such as electrode 116. In this embodiment, electrode 250A is the RV tip electrode, electrodes 250B and 250C are the same RV coil electrode, and electrode 250D is the SVC coil electrode. In one embodiment, the SVC coil electrode is electrically connected to the can electrode. Defibrillation circuit 234 includes a shock channel 244 to deliver cardioversion/defibrillation pulses (shocks). In the illustrated embodiment, shock channel 244 delivers the shocks using the same pair of electrodes as used by morphology channel 242 (so the "morphology channel" is also referred to as the "shock channel"). In an alternative embodiment, a single cardiac signal is sensed for use in heart rate detection and morphology analysis, such as through electrodes 250C and 250D. While this alternative embodiment eliminates the need for sensing two cardiac signals, the embodiment as illustrated in FIG. 2 provides for an easier heart beat detection. Implant control circuit 236 controls the operation of IMD 205 including the sensing of the one or more cardiac signals and the delivery of the shocks. Implant telemetry circuit 238 supports the functions of telemetry link 185, including transmitting the cardiac data from IMD 205 to external system 290.

External system 290 represents an embodiment of external system 190 and includes arrhythmia classification system 130, an external telemetry circuit 248, and a user interface 254. Implant telemetry circuit 248 supports the functions of telemetry link 185, including receiving the cardiac data transmitted from IMD 205. User interface 254 includes a user input device 256 and a presentation device 258. User input device 256 receives various commands and parameters from the user for controlling operations of IMD 205 and external system 290. Presentation device 258 presents various patient and device information including the episode information generated by arrhythmia classification system 130.

Figure 3:
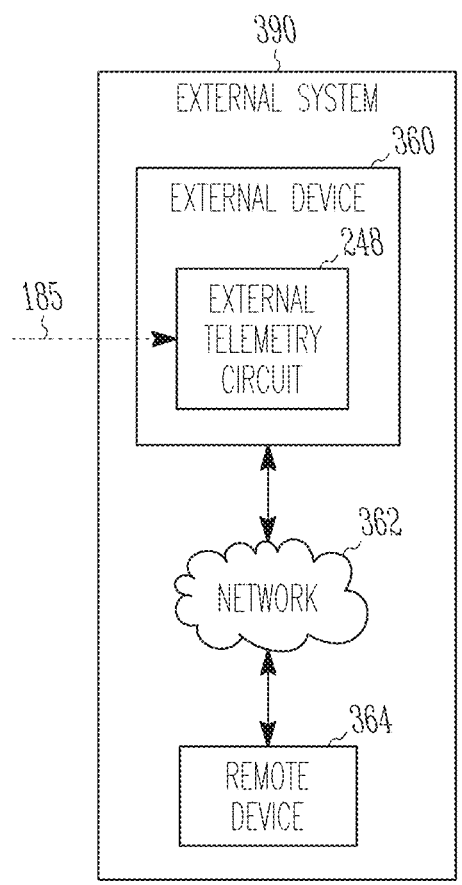
FIG. 3 is a block diagram illustrating an embodiment of the external system.

FIG. 3 is a block diagram illustrating an embodiment of an external system 390. External system 390 represents an embodiment of external system 290. In the illustrated embodiment, external system 390 is a patient management system including an external device 360, a telecommunication network 362, and a remote device 364. External device 360 is to be placed within the vicinity of IMD 205 and includes external telemetry circuit 248 to communicate with IMD 205 via telemetry link 185. Remote device 364 is in one or more remote locations and communicates with external device 360 through network 362, thus allowing the user to monitor and treat a patient from a distant location and/or allowing access to various treatment resources from the one or more remote locations. In one embodiment, after the implantation of IMD 205, external system 390 allows the user to adjust settings of IMD 205 and monitor the patient using data acquired by IMD 205, including the cardiac data.

In various embodiments, external system 390 is a computer-based or microprocessor-based system. In various embodiments, arrhythmia classification system 130 is distributed in external device 360, remote device 364, or both external device 360 and remote device 364. In various embodiments, either one or both of external device 360 and remote device 364 include a user interface such as user interface 254.

Figure 4:
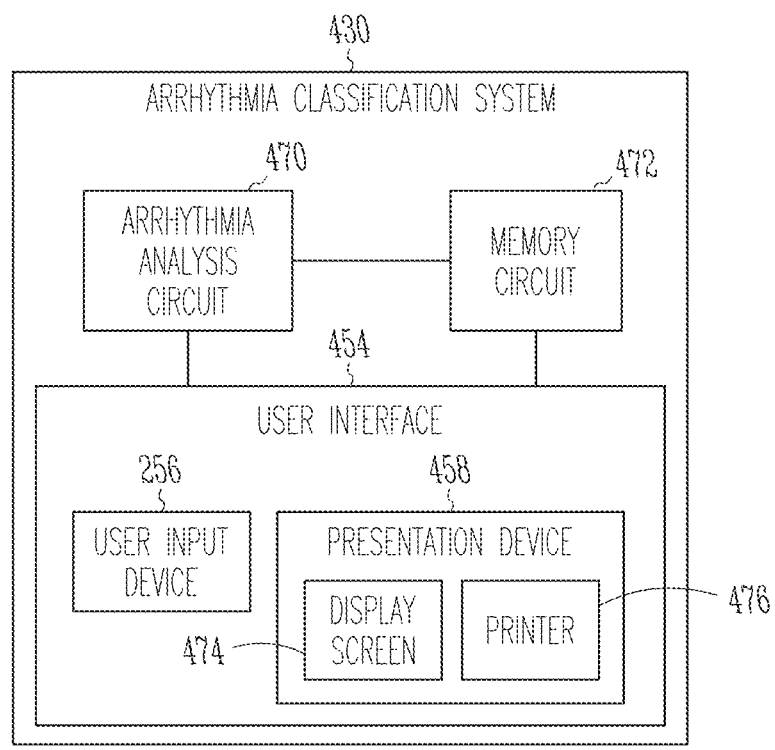
FIG. 4 is a block diagram illustrating an embodiment of portions of an arrhythmia classification system in the external system.

FIG. 4 is a block diagram illustrating an embodiment of portions of an arrhythmia classification system 430, which represents an embodiment of arrhythmia classification system 130. Arrhythmia classification system 430 includes an arrhythmia analysis circuit 470, a memory circuit 472, and a user interface 454.

Arrhythmia analysis circuit 470 receives the cardiac data transmitted from IMD 205, performs automatic adjudication of each episode of one or more arrhythmia episodes using the cardiac data, and generates episode data representative of information associated with the each episode. The information associated with the each episode includes an episode classification resulting from the automatic adjudication of the each episode and a confidence level in the episode classification. The episode classification is a classification for the each episode that indicates a type and an origin of the each episode. In one embodiment, the information associated with the each episode further includes episode features including key features rationalizing the automatic adjudication of the each episode. Memory circuit 472 stores data including the cardiac data and the episode data. User interface 454 represents an embodiment of user interface 254 and includes user input device 256 and a presentation device 458. Presentation device 458 presents the information associated with the each episode. In the illustrated embodiment, presentation device 458 includes a display screen 474 and a printer 476.

Figure 5:
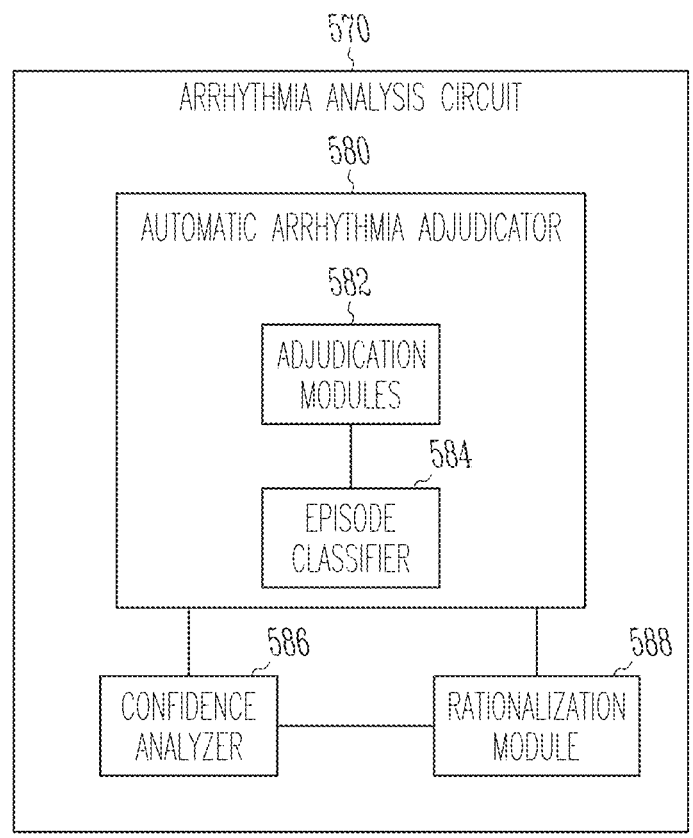
FIG. 5 is a block diagram illustrating an embodiment of an arrhythmia analysis circuit of the arrhythmia classification system.

FIG. 5 is a block diagram illustrating an embodiment of an arrhythmia analysis circuit 570. Arrhythmia analysis circuit 570 represents an embodiment of arrhythmia analysis circuit 470 and includes an automatic arrhythmia adjudicator 580, a confidence analyzer 586, and a rationalization module 588. Automatic arrhythmia adjudicator 580 determines the episode classification for each arrhythmia episode using the cardiac data by executing a plurality of adjudication algorithms. As illustrated in FIG. 5, automatic arrhythmia adjudicator 580 includes a plurality of adjudication modules 582 and an episode classifier 584. Adjudication modules 582 each determine a voting classification for the episode by executing an adjudication algorithm of the plurality of adjudication algorithms. Episode classifier 584 determines the episode classification for the episode using the voting classifications produced by executing the plurality of adjudication algorithms. The adjudication algorithms are each selected from available machine learning algorithms each implementing a tachyarrhythmia adjudication algorithm. In various embodiments, machine learning algorithms known to produce reasonably accurate results in arrhythmia classification are selected to be included in the plurality of adjudication algorithms. Some examples of such machine learning algorithms include support vector machine (SVM), decision tree learning, Bayesian machine learning, and outlier detection (such as Mahalanobis distance-based outlier detection). Examples of suitable machine learning algorithms are also discussed in Ian H. Witten, Eibe Frank, and Mark A. Hall, *Data Mining: Practical Machine Learning Tools and Techniques*. Third Edition, Burlington, Mass.: Morgan Kaufmann, 2011. An example of decision tree learning is discussed below with reference to FIG. 9. An example of automatic arrhythmia adjudicator 580 is discussed in U.S. Patent Application Publication No. US 2010/0280841 A1, entitled "ADJUDICATION OF ARRHYTHMIA EPISODE DATA SYSTEMS AND METHODS", assigned to Cardiac Pacemakers, Inc., which is incorporated herein by reference in its entirety. Confidence analyzer 586 determines the confidence level in the episode classification using the voting classifications. The confidence level depends on consistency among the voting classifications produced by executing the plurality of adjudication algorithms.

In one embodiment, episode classifier 584 determines the episode classification for the episode using one or more primary voting classifications produced by executing one or more primary adjudication algorithms, and confidence analyzer 586 determines the confidence level in the episode classification using one or more secondary voting classifications produced by one or more secondary adjudication algorithms. The one or more primary adjudication algorithms are selected from the plurality of adjudication algorithms, and the one or more secondary adjudication algorithms are selected from the remaining algorithms of the plurality of adjudication algorithms. In various embodiments, the one or more primary adjudication algorithms include one or more machine learning algorithms known to produce acceptable results in implementing the tachyarrhythmia adjudication algorithm. The confidence level is proportional to the number of voting classification(s) produced by the one or more secondary adjudication algorithms that is(are) consistent with the episode classification. In one embodiment, episode classifier 584 determines the episode classification using the voting classification produced by one primary adjudication algorithm, such as one implemented by support vector machine using radial basis function (SVM-RBF). Confidence analyzer 586 determines the confidence level in the episode classification using secondary voting classifications produced by a plurality of secondary adjudication algorithms. The amount (number) of machine learning algorithms to be included in the plurality of secondary algorithms is determined based on one or more estimated measures of accuracy in the automatic adjudication and an estimated potential need for manual adjudication by the user, as further discussed below. In another embodiment, episode classifier 584 determines the episode classification based on a majority voting using the primary voting classifications produced by a plurality of primary adjudication algorithms. Confidence analyzer 586 determines the confidence level in the episode classification using the secondary voting classifications produced by a plurality of secondary adjudication algorithms.

In another embodiment, episode classifier 584 determines the episode classification for the episode based on a majority voting using selected voting classifications produced by executing the plurality of adjudication algorithms. Confidence analyzer 586 determines the confidence level in the episode classification also using the selected voting classifications. The confidence level is indicative of a percentage of voting classifications consistent with the episode classification. The selected voting classification includes all of a specified number of the voting classifications produced by the plurality of adjudication algorithms.

In one embodiment, confidence analyzer 586 produces the determined confidence level as a ratio or percentage. In other embodiments, the confidence level as presented to the user is a function of the ratio or percentage. In one embodiment, confidence analyzer 586 produces the determined confidence level as a parameter having discrete or continuous numerical values. In another embodiment, the confidence level as presented to the user includes a parameter having a set of discrete values, such as high and low, or high, medium, and low, that are determined using the actual ratio and one or more threshold values.

In various embodiments, the amount (number) of voting classifications used to determine the episode classification and the confidence level in the episode classification is determined based on one or more estimated measures of accuracy in the automatic adjudication and an estimated potential need for manual adjudication by the user. An arrhythmia episode with an episode classification identified with a high confidence level is unlikely to be examined by the user and manually adjudicated. An arrhythmia episode with a classification identified with a low confidence level needs to be examined by the user, i.e., needs to be manually adjudicated. Examples of the estimated measures include a risk factor, a specificity factor, and a service burden factor. The risk factor is a proportion of arrhythmia episodes with classification identified as high confidence classifications that are misclassified during the automatic adjudication to a total number of classified arrhythmia episodes. The risk factor indicates the chance of a high confidence classification that is actually an incorrect classification. The specificity factor is a proportion of misclassified arrhythmia episodes with classifications identified as low confidence classifications to the total number of classified arrhythmia episodes. The specificity factor indicates the chance of a low confidence classification that is actually an incorrect classification. The service burden factor is a proportion (e.g., a percentage) of arrhythmia episodes with classification identified as low confidence classifications to the total number of classified arrhythmia episodes. The service burden factor indicates the chance of an episode being classified with a low-confidence level and hence needs to be manually adjudicated. Results from an evaluation of these factors, each as a function of the number of machine learning algorithms included in the automatic arrhythmia adjudication, are presented in FIG. 11.

Figure 10:
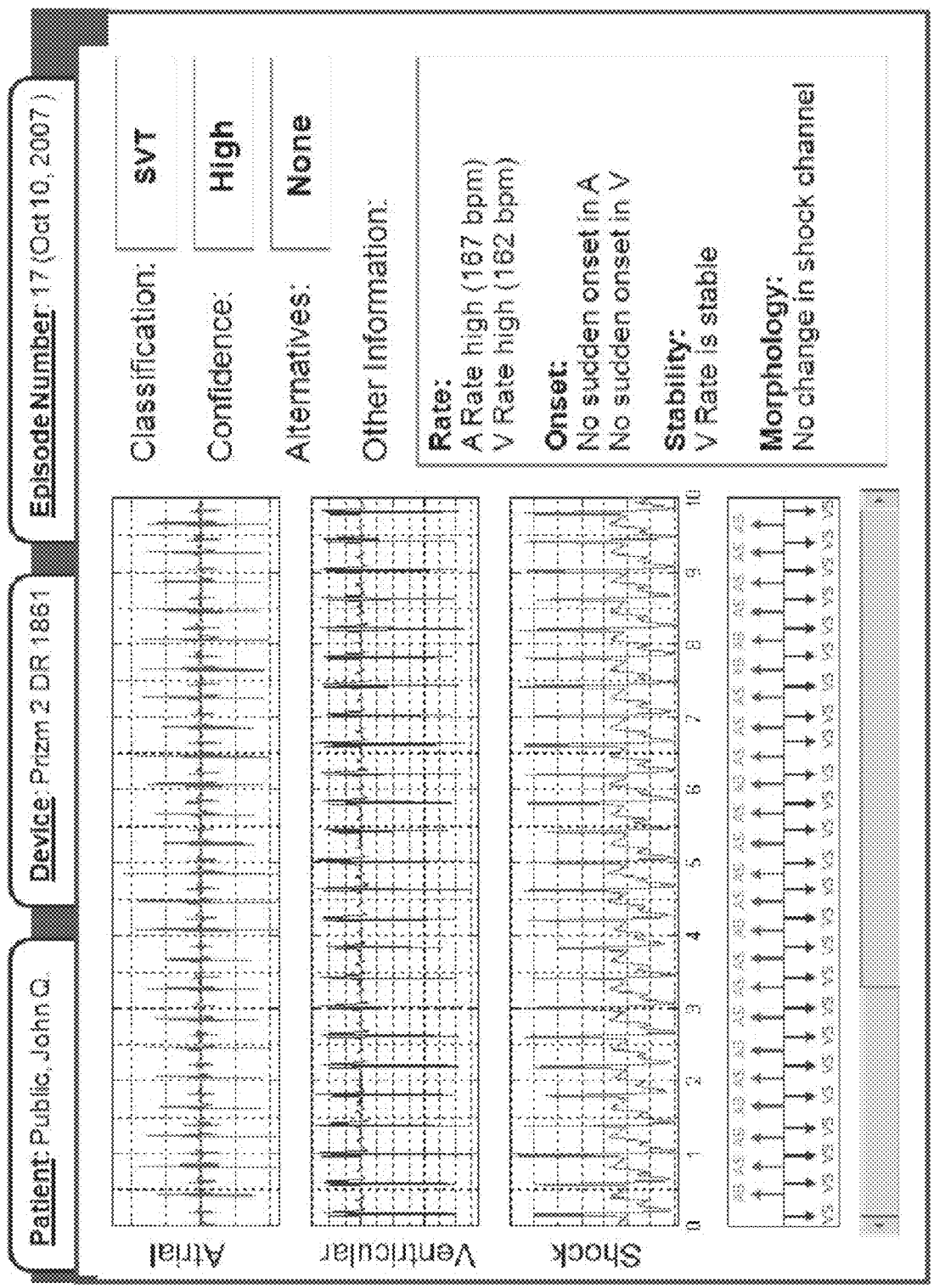
FIG. 10 is an illustration of an example of a display screen presenting information associated with an arrhythmia episode.

Rationalization module 588 generates episode features including key features rationalizing the automatic adjudication of each arrhythmia episode. The key features indicate the basis upon which the episode classification results from the automatic arrhythmia adjudication. In one embodiment, the episode features also include additional features that are not used in the automatic adjudication but may be useful in the manual adjudication of the arrhythmia episode. Examples of the episode features include (1) heart rates during the episode such as atrial rate, ventricular rate, and average atrial and ventricular rates during a specified number of the fastest beats; (2) atrioventricular (AV) rate relationship during the episode, such as whether the atrial rate approximately equals the ventricular rate (1:1 tachyarrhythmia) and the leading channel (the channel with the highest rate) when the atrial rate substantially differs from the ventricular rate; (3) onset of the episode, such as whether and when atrial sudden onset is detected, whether and when ventricular sudden onset is detected, whether and when premature ventricular contraction (PVC) detected at the onset of the episode, whether and when the onset of the episode is detected in each of the atrial and ventricular channels, and whether atrial onset or ventricular onset is first detected; (4) rate stability during the episode, such as ventricular rate stability; and (5) morphology of cardiac signal(s) during the episode, such as whether change in shock channel signal morphology is detected and whether a highly variable shock channel signal morphology is detected. In various embodiments, the information associated with the each episode, including the episode classification, the confidence level, and the episode features, is presented to the user to allow for review of the automatic adjudication of each arrhythmia episode by the user and/or manual adjudication of each arrhythmia episode by the user. An example of display screen 474 presenting such information is illustrated in FIG. 10. In another embodiment, arrhythmia analysis circuit 470 or 570 uses a fuzzy logic rule base to provide rationale for classifying the arrhythmia episode. Rationalization module 588 generates information related to decision making leading to the episode classification.

In one embodiment, arrhythmia analysis circuit 470 or 570 includes portions of a processor circuit, such as a microprocessor, a microcontroller, or a custom integrated circuit, that are programmed to perform the automatic arrhythmia adjudication, confidence level determination, and episode feature determination functions discussed in this document. Each element of arrhythmia analysis circuit 570 as illustrated in FIG. 5 includes a portion of the processor circuit programmed to perform the function of that element as discussed in this document.

Figure 6:
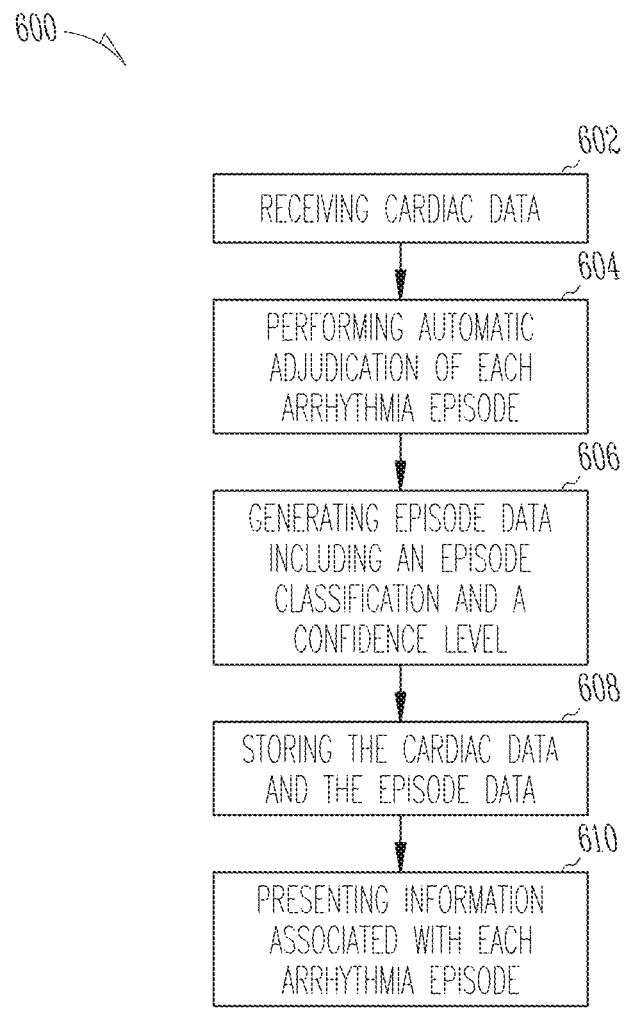
FIG. 6 is a flow chart illustrating an embodiment of a method for classifying cardiac arrhythmias.

FIG. 6 is a flow chart illustrating an embodiment of a method 600 for classifying cardiac arrhythmias. In one embodiment, method 600 is performed using CRM system 100, including the various embodiments of its elements discussed in this document. In one embodiment, arrhythmia classification system 130, including the various embodiments of its elements discussed in this document, is programmed to perform method 600.

At 602, cardiac data are received from an IMD such as an ICD. The cardiac data are representative of the one or more cardiac signals sensed by the IMD. The one or more cardiac signals are indicative of one or more arrhythmia episodes of a patient in whom the IMD is implanted.

At 604, automatic adjudication of each episode of one or more arrhythmia episodes is performed using the cardiac data. An episode classification is determined for the episode using the cardiac data by executing a plurality of adjudication algorithms. The episode classification is a classification for the episode that indicates a type and an origin of the episode. The plurality of adjudication algorithms includes machine learning algorithms each selected to implement a tachyarrhythmia adjudication algorithm.

At 606, episode data are generated. The episode data are representative of information associated with the episode, and includes an episode classification resulting from the automatic adjudication of the episode and a confidence level in the episode classification. In one embodiment, the information associated with the episode further includes episode features including key features rationalizing the automatic adjudication of the each episode. The key features allow the user to manually adjudicate the episode, such as when the confidence level in the episode classification is low.

At 608, the cardiac data and the episode data are stored in a memory device. At 610, the information associated with the episode is presented to the user. This allows the user to review the patient's conditions including the one or more arrhythmia episodes. In various embodiments, portions of the cardiac data and the episode data are presented simultaneously using a display screen. An example of such a presentation is illustrated in FIG. 10.

Figure 7:
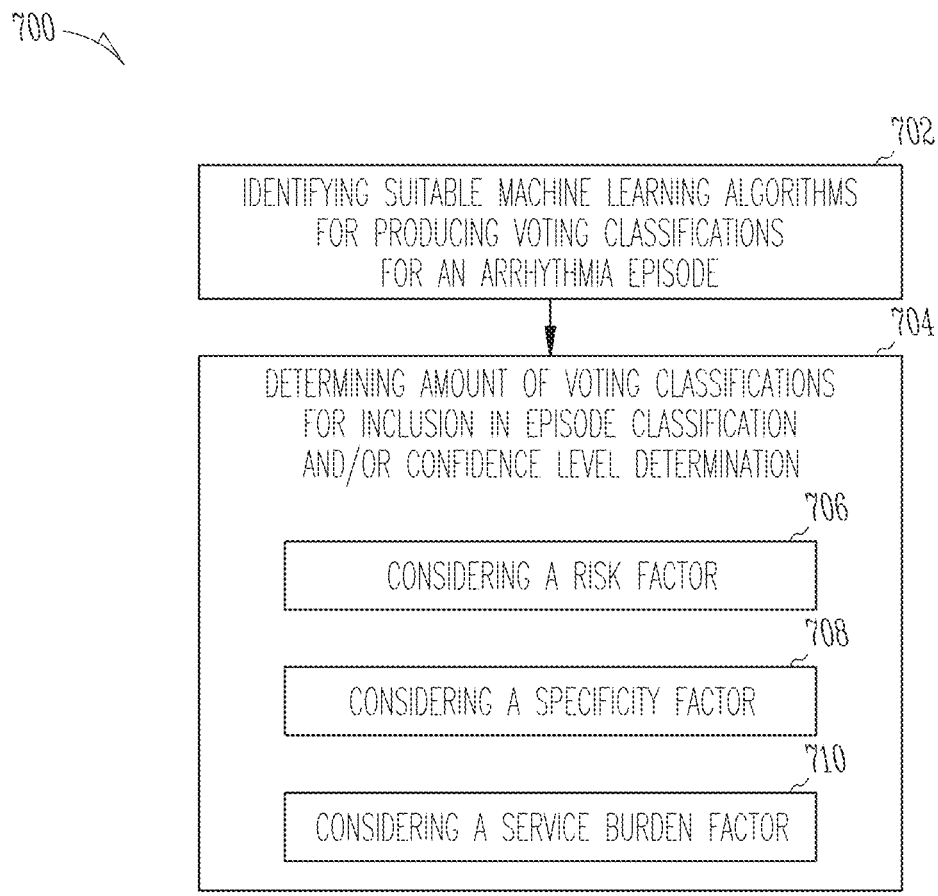
FIG. 7 is a flow chart illustrating an embodiment of a method for selecting machine learning algorithms for performing automatic arrhythmia adjudication.

FIG. 7 is a flow chart illustrating an embodiment of a method 700 for selecting machine learning algorithms and voting classifications produced by executing the selected machine learning algorithms for determination of the episode classification of an arrhythmia episode and the confidence level in the episode classification. Method 700 is used to select the plurality of adjudication algorithms for use in method 600.

At 702, suitable machine learning algorithms are identified for implementing a tachyarrhythmia adjudication algorithm. To automatically adjudicate the arrhythmia episode, the identified machine learning algorithms are each executed to generate a voting classification for the arrhythmia episode. At 704, the amount (number) of voting classifications (decisions) produced by these machine learning algorithms to be included in determining the episode classification for the arrhythmia episode and/or the confidence level in the episode classification is determined based on one or more estimated measures of accuracy in the automatic arrhythmia adjudication and an estimated potential need for manual adjudication by the user. In the illustrated embodiment, the amount of machine learning algorithms is determined based on the risk factor, the specificity factor, and the service burden factor as discussed above with reference to FIG. 5. At 706, the risk factor is considered. At 708, the specificity factor is considered. At 710, the service burden factor is considered. In various embodiments of method 700, any one or more steps selected from 706, 708, and 710 are performed. The amount of classifications produced by the machine learning algorithms to be included in determining the episode classification and/or the confidence level in the episode classification is determined by balancing the performance (accuracy of arrhythmia classification) with the cost (system complexity and user time).

Figure 8:
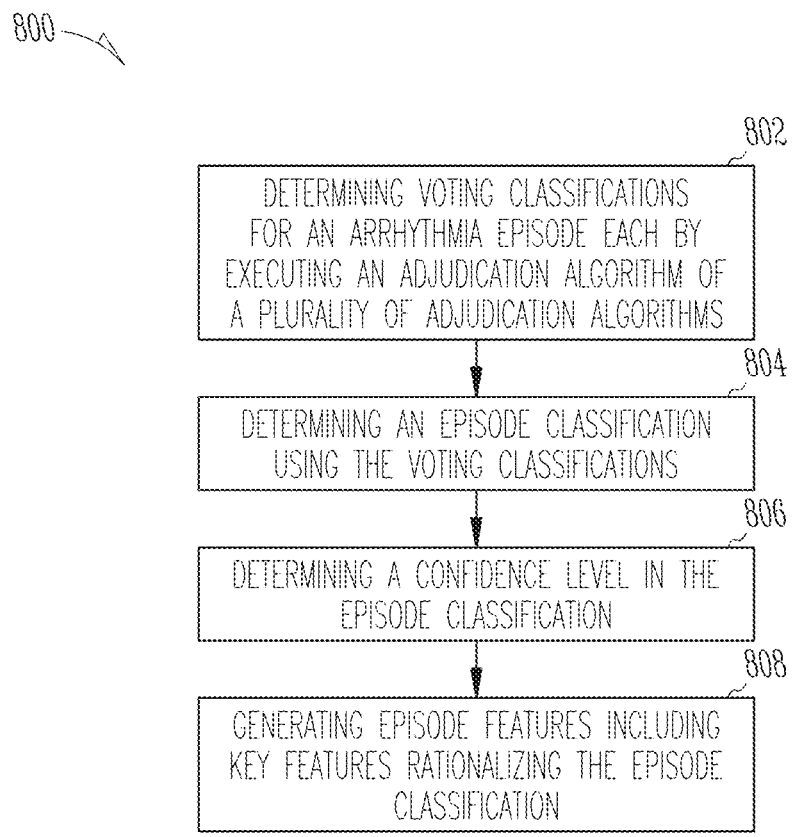
FIG. 8 is a flow chart illustrating an embodiment of a method for generating episode data for each arrhythmia episode.

FIG. 8 is a flow chart illustrating an embodiment of a method 800 for generating episode data for each arrhythmia episode. Method 800 represents an embodiment of part of method 600 including steps 604 and 606. In one embodiment, arrhythmia analysis circuit 470, including the various embodiments of its elements discussed in this document, is programmed to perform method 800.

At 802, voting classifications for each arrhythmia episode are each determined by executing an adjudication algorithm of the plurality of adjudication algorithms. At 804, the episode classification is determined by one or more primary voting classifications selected from the voting classifications produced by executing the plurality of adjudication algorithms. At 806, the confidence level in the episode classification is determined using one or more secondary voting classifications selected from the voting classifications produced by executing the plurality of adjudication algorithms. In one embodiment, the one or more primary voting classifications and the one or more secondary voting classifications include one or more voting classifications produced by the same adjudication algorithm(s) selected from the plurality of adjudication algorithms. In another embodiment, the one or more primary voting classifications and the one or more secondary voting classifications include voting classifications produced by the different adjudication algorithm selected from the plurality of adjudication algorithms.

At 808, episode features rationalizing the episode classification are generated. In one embodiment, the episode features include features used to determine the episode classification by executing the plurality of adjudication algorithms. In one embodiment, the episode features include features allowing for manual adjudication of the episode. In various embodiments, the episode data are included in the information associated with the episode to be stored and presented to the user.

Figure 9:
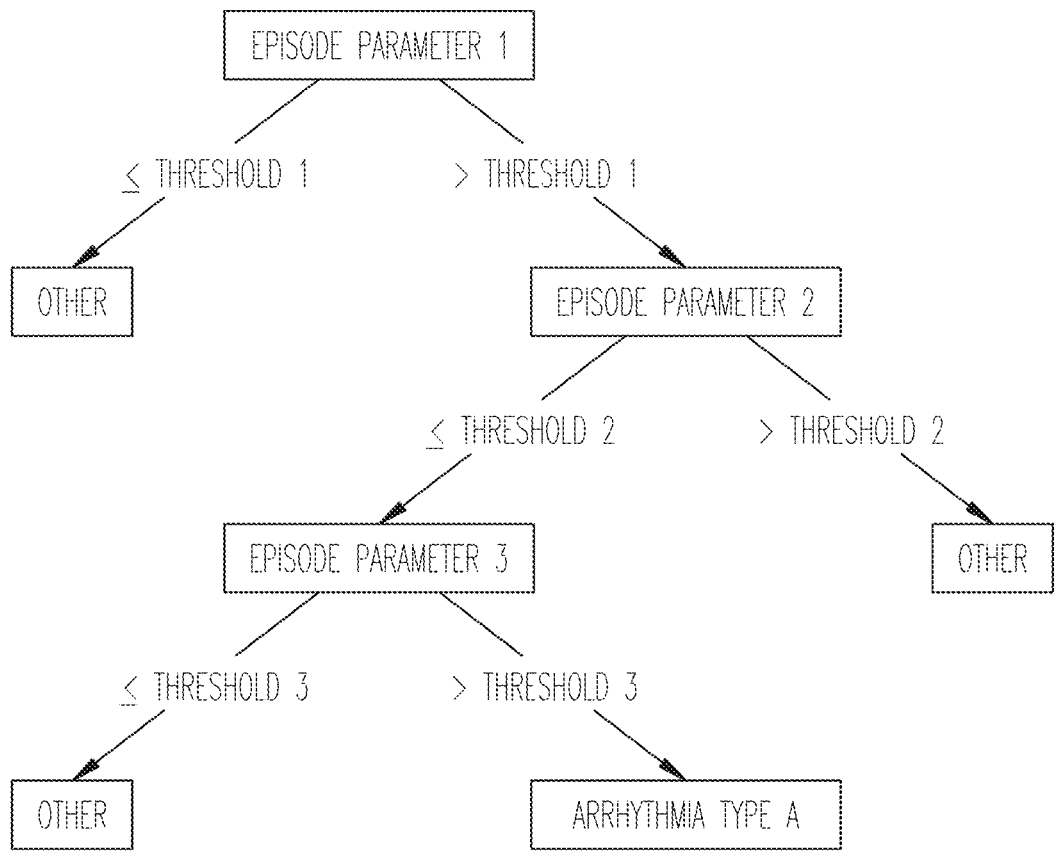
FIG. 9 is a flow chart illustrating an embodiment of a method of decision tree learning.

FIG. 9 is a flow chart illustrating an embodiment of a method for decision tree learning referred to as "one-versus-all" decision tree. The illustrated decision tree is for determining whether a detected arrhythmia episode is of a particular type designated as "arrhythmia type A" for illustrative purposes. Three episode parameters (episode parameters 1, 2, and 3) each indicating one or more characteristics of arrhythmia type A are determined from one or more cardiac signals indicative of the detected arrhythmia episode. Episode parameters 1, 2, and 3 each have a predetermined threshold value (thresholds 1, 2, and 3). Each episode parameter is compared to its threshold value. The outcome of the comparison determines whether the detected arrhythmia episode is not an arrhythmia type A (i.e., "other") or the next episode is to be compared to its threshold value until all the episode parameters are compared. Examples of "arrhythmia type A" include ventricular fibrillation (VF), ventricular tachycardia (VT), supraventricular tachyarrhythmia (SVT), atrial fibrillation (AF), atrial flutter (AFL), sinus tachycardia (ST), and atrial tachycardia (AT). Examples of the episode parameters include an atrial rate, a ventricular rate, an onset rate indicating whether the detected arrhythmia episode has a gradual onset or a sudden onset, a stability parameter indicative of a degree of ventricular rate variability, and a correlation coefficient representative of a morphological correlation between a waveform of a cardiac signal during the detected arrhythmia episode and a template waveform being a waveform of the cardiac signal during a known cardiac rhythm.

FIG. 10 is an illustration of an example of a display screen presenting information associated with an arrhythmia episode. In various embodiments, the display screen is part of an external system for communicating with an IMD. One example of such a display screen is display screen 474. In various other embodiments, the display screen of part of any computer or computer-based system used to analyze cardiac data representing cardiac signals indicative of one or more arrhythmia episodes.

The presented information associated with an arrhythmia episode as illustrated in FIG. 10 includes:
  intracardiac electrograms:
    atrial electrogram ("Atrial");
    ventricular electrogram sensed though a rate channel ("Ventricular"); and
    a ventricular electrogram sensed through shock channel (morphology channel) ("Shock");
  the episode classification ("Classification");
  the confidence level in the episode classification ("Confidence");
  the alternative episode classification ("Alternative") ("None" value unless the confidence level is low);
  episode features including key features rationalizing the automatic adjudication of the each episode ("Other Information");
    heart rates during the episode ("Rate"):
      atrial rate; and
      ventricular rate;
    onset of the episode (Onset"):
      whether onset as detected in an atrium is sudden; and
      whether onset as detected in a ventricle is sudden;
    stability {"Stability"):
      whether ventricular rate is stable; and
    morphology (Morphology):
      whether morphology of the cardiac signal sensed through the shock channel changes;

Various types of information are presented in FIG. 10 by way of example, and not by way of limitation. In various embodiments, the information associated with an arrhythmia episode may include any combination of such information as discussed in this document and any other information that is available and interested by the user for the purpose of performing monitoring, diagnosis, and/or treatment of the patient.

Figure 11:
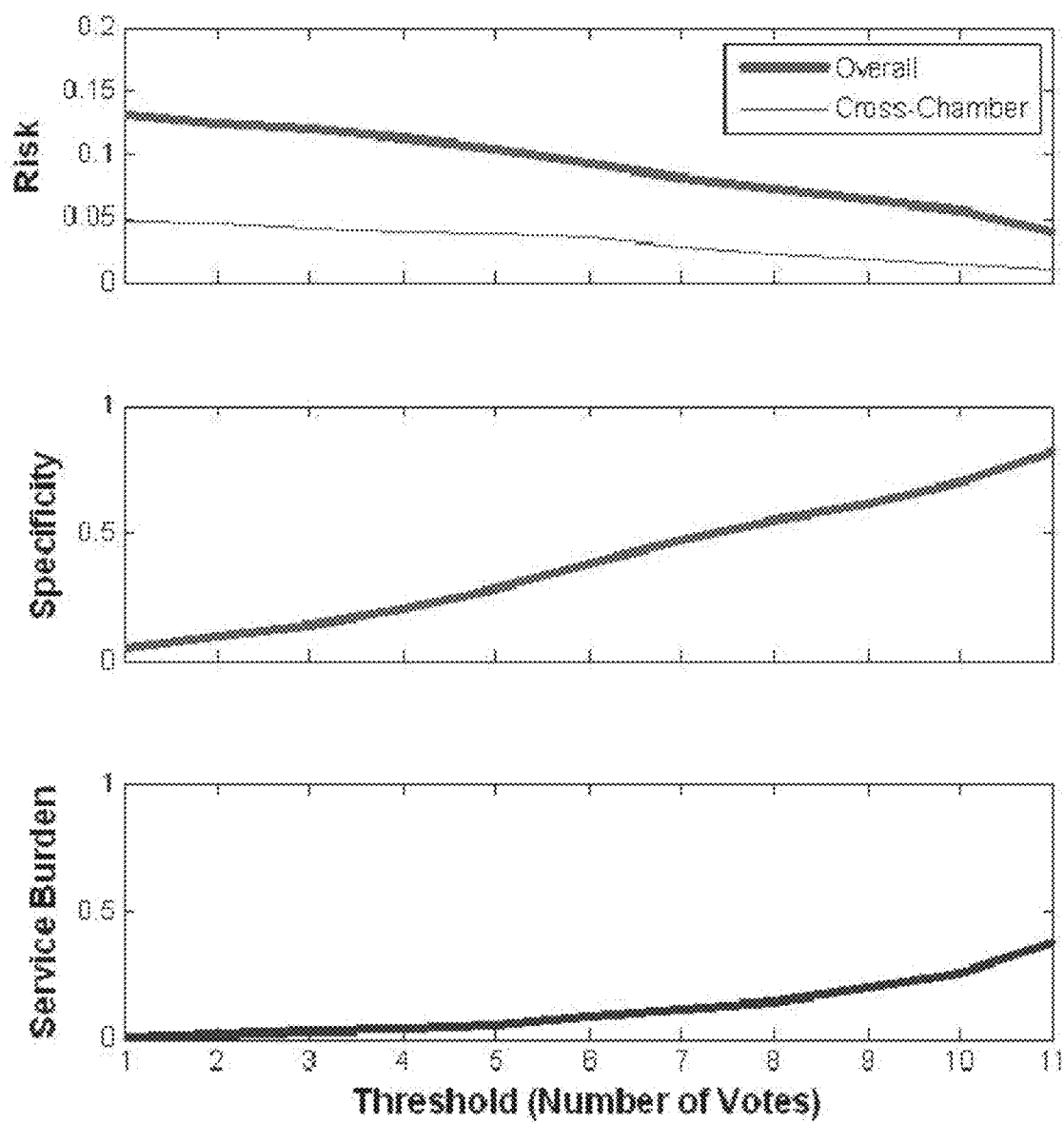
FIG. 11 includes graphs illustrating an example of various factors considered in selecting machine learning algorithms for the automatic arrhythmia adjudication.

FIG. 11 includes graphs illustrating an example of various factors considered in selecting machine learning algorithms for automatic adjudication of arrhythmia episodes. The risk, specificity, and service burden factors are each evaluated with a plurality of machine learning algorithms implementing a tachyarrhythmia adjudication algorithm. The graph for the risk factors shows that the chance for a high confidence classification to be actually an incorrect classification decreases with the number of machine learning algorithms used. The graph of the specificity factor shows that the chance of a low confidence classification to be actually an incorrect classification increases with the number of machine learning algorithms used. The graph of the service burden factor shows that the percentage of arrhythmia episodes that needs to be manually reviewed increases with the number of machine learning algorithms used. Such graphs provide a basis for determining the number of classifications produced by machine learning algorithms to be included for determining the episode classification for an arrhythmia episode and/or the confidence level in the episode classification by balancing the benefit (accuracy of arrhythmia classification) and cost (system cost and user time for manual analysis).

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system configured to be communicatively coupled to an implantable medical device sensing one or more cardiac signals indicative of one or more arrhythmia episodes and produce cardiac data representative of the one or more cardiac signals, the system comprising:
  an arrhythmia analysis circuit configured to receive cardiac data transmitted from the implantable medical device, perform automatic adjudication of each episode of one or more arrhythmia episodes using the cardiac data by executing a plurality of adjudication algorithms to produce voting classifications for each episode, determining a voting classification of the voting classifications for each episode by executing an adjudication algorithm of the plurality of adjudications algorithms, determining an episode classification for each episode using one or more primary voting classifications selected from the voting classifications and a confidence level in the episode classification based on the voting classifications for each episode, and generate episode data representative of information associated with each episode including the episode classification and the confidence level in the episode classification;
  a memory circuit configured to store data including the cardiac data and the episode data; and
  a user interface including a presentation device configured to present the information associated with each episode.

2. The system of claim 1, wherein the arrhythmia analysis circuit comprises an automatic arrhythmia adjudicator configured to execute the adjudication algorithms each being a machine learning algorithm implementing a tachyarrhythmia adjudication algorithm.

3. The system of claim 1, wherein the arrhythmia analysis circuit comprises a confidence analyzer configured to determine the confidence level in the episode classification using one or more secondary voting classifications selected from the voting classifications produced by executing the plurality of adjudication algorithms, the confidence level indicative of a percentage of the one or more secondary voting classifications consistent with the episode classification.

4. The system of claim 1, comprising an external telemetry circuit configured to receive the cardiac data from the implantable medical device.

5. The system of claim 4, comprising an external device including the external telemetry circuit, a remote device including at least the user interface, and a communication network coupling between the external device and the remote device.

6. A system configured to be communicatively coupled to an implantable medical device sensing one or more cardiac signals indicative of one or more arrhythmia episodes and produce cardiac data representative of the one or more cardiac signals, the system comprising:

an arrhythmia analysis circuit configured to receive cardiac data transmitted from the implantable medical device, perform automatic adjudication of each episode of one or more arrhythmia episodes using the cardiac data, and generate episode data representative of information associated with each episode including an episode classification resulting from the automatic adjudication of each episode, a confidence level in the episode classification, and episode features including key features rationalizing the automatic adjudication of each episode;

a memory circuit configured to store data including the cardiac data and the episode data; and a user interface including a presentation device configured to present the information associated with each episode, wherein the arrhythmia analysis circuit is configured to determine the episode classification for each episode and the confidence level in the episode classification using the cardiac data by executing a plurality of adjudication algorithms.

7. The system of claim 6, wherein the arrhythmia analysis circuit comprises a rationalization module configured to generate episode features including features used by the automatic arrhythmia adjudicator to determine the episode classification for each episode.

8. The system of claim 7, wherein the rationalization module is configured to generate episode features including features allowing for manual adjudication of each episode.

9. The system of claim 6, wherein the arrhythmia analysis circuit comprises an automatic arrhythmia adjudicator configured to execute the adjudication algorithms each being a machine learning algorithm implementing a tachyarrhythmia adjudication algorithm.

10. The system of claim 6, comprising an external device including the external telemetry circuit configured to receive the cardiac data from the implantable medical device, a remote device including at least the user interface, and a communication network coupling between the external device and the remote device.

11. A method for classifying cardiac arrhythmias, the method comprising:
receiving cardiac data representative of the one or more cardiac signals sensed by an implantable medical device, the one or more cardiac signals indicative of one or more arrhythmia episodes;
performing automatic adjudication of each episode of one or more arrhythmia episodes using the cardiac data, including executing a plurality of adjudication algorithms to produce voting classifications for each episode and determining an episode classification for each episode and a confidence level in the episode classification based on the voting classifications for each episode;
generating episode data representative of information associated with each episode including the episode classification, the confidence level in the episode classification and episode features including key features rationalizing the automatic adjudication of each episode;
storing the cardiac data and the episode data in a memory device; and
presenting the information associated with each episode.

12. The method of claim 11, wherein the plurality of adjudication algorithms comprises machine learning algorithms each selected to implement a tachyarrhythmia adjudication algorithm.

13. The method of claim 12, comprising determining an amount of machine learning algorithms to be included in the plurality of adjudication algorithms based on one or more estimated measures of accuracy in the automatic adjudication and an estimated potential need for manual adjudication by a user.

14. The method of claim 13, comprising determining the amount of machine learning algorithms to be included in the plurality of adjudication algorithms based on one or more factors selected from:
a risk factor being a proportion of arrhythmia episodes with classification identified as high confidence classifications that are misclassified during the automatic adjudication to a total number of classified arrhythmia episodes;
a specificity factor being a proportion of misclassified arrhythmia episodes with classifications identified as low confidence classifications to the total number of classified arrhythmia episodes; and
a service burden factor being a proportion of arrhythmia episodes with classification identified as low confidence classifications to the total number of classified arrhythmia episodes.

15. The method of claim 11, wherein performing the automatic adjudication comprises:
determining a voting classification of the voting classifications for each episode by executing an adjudication algorithm of the plurality of adjudication algorithms; and
determining the episode classification using one or more primary voting classifications selected from the voting classifications produced by executing the plurality of adjudication algorithms.

16. The method of claim 15, comprising determining the confidence level in the episode classification using one or more secondary voting classifications selected from the voting classifications produced by executing the plurality of adjudication algorithms, the confidence level indicative of a percentage of the one or more secondary voting classifications consistent with the episode classification.

17. The method of claim 11, comprising generating episode features including features used to determine the episode classification during the automatic adjudication of each episode.

18. The method of claim 17, comprising generating episode features including features allowing for manual adjudication of each episode.

* * * * *